United States Patent [19]

Bauer et al.

[11] Patent Number: 4,902,826
[45] Date of Patent: Feb. 20, 1990

[54] PROCESS FOR THE PREPARATION OF 2-ARYLTHIOBENZOIC ACIDS

[75] Inventors: Wolfgang Bauer, Maintal; Manfred Langer; Kuno Reh, both of Frankfurt, all of Fed. Rep. of Germany

[73] Assignee: Bayer Aktiengesellschaft, Leverkusen-Bayerwerk, Fed. Rep. of Germany

[21] Appl. No.: 201,851

[22] Filed: Jun. 3, 1988

[30] Foreign Application Priority Data

Jul. 11, 1987 [DE] Fed. Rep. of Germany ....... 3723079

[51] Int. Cl.$^4$ ............................................. C07C 149/40
[52] U.S. Cl. .................................................... 562/432
[58] Field of Search .................. 562/432, 493; 560/18; 568/65, 67

[56] References Cited

U.S. PATENT DOCUMENTS 2,951,082  8/1960  Sprague et al. ..................... 562/432
4,094,900  6/1978  Anderson et al. .................. 562/474

OTHER PUBLICATIONS

The Condensed Chemical Dictionary, 10th Ed., Rev. by G. G. Hawley, Van Nostrand Reinhold Company, N.Y., 1981, p. 31.

Primary Examiner—Michael L. Shippen
Attorney, Agent, or Firm—Connolly and Hutz

[57] ABSTRACT

A process for the preparation of 2-arylthiobenzoic acids which are useful as intermediates in producing thioxanthene compounds comprises reacting by reacting lithium 2-chlorobenzoate of the formula

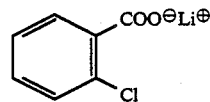

with lithium thiophenoxide of the formula

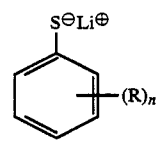

wherein
R is alkyl having 1 to 4 carbon atoms, alkoxy having 1 to 4 carbon atoms, trifluoromethyl, hydrogen, fluorine, chlorine or nitro and
n is 1, 2, 3 or 4.

14 Claims, No Drawings

PROCESS FOR THE PREPARATION OF 2-ARYLTHIOBENZOIC ACIDS

The present invention relates to a new process for the preparation of 2-arylthiobenzoic acids of the formula 1

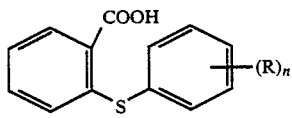  (I)

wherein

R denotes alkyl having 1 to 4 carbon atoms, alkoxy having 1 to 4 carbon atoms, trifluoromethyl, hydrogen, fluorine, chlorine or nitro and n denotes 1, 2, 3, or 4, where the R radicals can be identical or different, by reaction of lithium 2-chlorobenzoate of the formula II

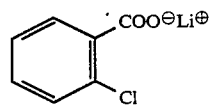  (II)

with lithium thiophenoxide of the formula III

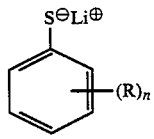  (III)

wherein R and n have the abovementioned meanings.

2-Arylthiobenzoic acids of the formula I are valuable intermediates for the preparation of thioxanthenes, which are used, for example, as photoinitiators for UV-hardening paints (M. J. Davis et al., J. Oil Col. Chem. Assoc. 61. 256 (1978)) or as starting compounds for strongly active neuroleptics (H. J. Roth and A. Kleemann, Pharmaceutische Chemie I, Arzneistoffsynthese, (Pharmaceutical Chemistry I, Synthesis of Medicaments), G. Thieme Verlag Stuttgart, 1982, pp. 284–286).

Various processes for the preparation of 2-arylthiobenzoic acids are already known, according to which 2-halogenobenzoic acids can be reacted with thiophenols.

For example, according to the procedure indicated in U.S. Pat. No. 4,094,900, sodium 2-chlorobenzoate reacts with sodium 4-chlorothiophenoxide in the presence of equimolar amounts of sodium iodide at 170° C. (7 hours) to give 2-(4-chlorophenylthio)benzoic acid. The disadvantage of this method lies in the use of equimolar amounts of sodium iodide, since this process is uneconomical owing to the high costs of sodium iodide. A high waste water loading additionally occurs owing to unrecovered sodium iodide.

An additional process known from the literature is given by the Ullmann reaction of 2-iodobenzoic acid with thiophenols in potassium hydroxide solution and in the presence of copper (J. O. Jilek et al., Collect. Czechoslov. Chem. Commun. 33, 1831 (1968), French Patent Specifications M. 6165, 5964) or by 2-chlorobenzoic acid with thiophenols in nitrobenzol in the presence of potassium carbonate and copper iodide and copper bronze as catalysts (J. D. Brindle et al., Can. J. Chem. 61, 1869 (1983)). These reactions exhibit as disadvantages the use of expensive starting materials such as 2-iodobenzoic acid and also the employment of copper or copper iodide. The use of copper as a catalyst in addition leads to the formation of by-products and therefore in itself to poorer yields of 2-arylthiobenzoic acids.

The present invention has the aim of making available a process for the preparation of 2-arylthiobenzoic acids, which does not exhibit the economic and ecological disadvantages of the indicated processes known from the literature.

This aim is surprisingly solved by reacting lithium 2-chlorobenzoate of the formula II with lithium thiophenoxide of the formula III.

In this way, the use of expensive catalysts such as equimolar amounts of sodium iodide, copper, copper iodide or the use of expensive educts such as 2-iodobenzoic acid can be avoided.

As a rule, the reaction is carried out at temperatures of 140° to 220° C., preferably at 170° to 200° C.

1 to 1.5 moles, preferably 1.1 to 1.3 moles, of chlorobenzoate are customarily employed per mole of thiophenoxide.

The process can either be carried out in the melt without the use of a solvent or in aprotic solvents at atmospheric pressure or under pressure in an autoclave.

Suitable solvents are, for example: toluene, o-, m-, p-xylene, mesitylene, chlorobenzene, o-chlorotoluene, o-dichlorobenzene, tetralin, solvent naphtha, dibutyl ether, diphenyl ether, dimethylformamide, dimethylacetamide, N-methylpyrrolidone, N,N-dimethylpropyleneurea, dimethyl sulfoxide and dimethylaniline.

The process according to the invention can be carried out in an advantageous manner by mixing 2-chlorobenzoic acid of the formula IV

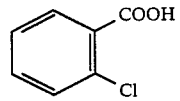  (IV)

and a thiophenol of the formula V

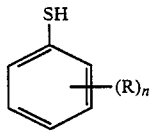  (V)

wherein R and n have the meanings already mentioned, if appropriate in a suitable solvent, converting into the corresponding lithium salts (formula II or III) using molar amounts of lithium hydroxide and/or lithium carbonate and/or lithium phosphate and removing the water of reaction by distillation at atmospheric pressure or in vacuo and subsequently heating to the desired reaction temperature. The reaction is normally complete in 2 to 8 hours.

After completion of the reaction, the resultant lithium 2-arylthiobenzoate of the formula VI

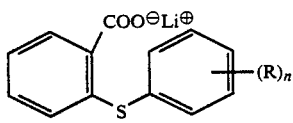

is taken up in water and converted into the free acid (formula I) using a mineral acid. Suitable mineral acids are, for example, hydrochloric acid, sulfuric acid and phosphoric acid.

The aqueous phase containing the compound of the formula VI is separated from the organic phase by the use of solvents which are immiscible or poorly miscible with water, by means of which the organic phase can be employed again without a further purification operation for following preparations.

If aprotic, water-miscible solvents are employed, these are removed by distillation before the addition of water.

The R radicals mentioned in the general formulae I, III and V can be identical or different. They can substitute the 2-, 3-, 4- and 5-positions of the aromatic ring. The 2-, 3- and 4-positions are preferred for n=1. The 4-position is very particularly preferred.

For n=2, the R substituents can be in the 2,3-, 2,4-, 2,5-, 3,4-, 3,5- and 4,5-position. For n=3, all conceivable combinations are also possible, the 2,4,5-substitution being preferred.

Thiophenols of the formula V which may be employed according to the process according to the invention are, for example: thiophenol, 4-fluorothiophenol, 3-fluorothiophenol, 4-chlorothiophenol, 2-chlorothiophenol, 2,5-dichlorothiophenol, 4-chloro-2,5-dimethylthiophenol, 4-methylthiophenol, 4-isopropylthiophenol, 3-trifluoromethylthiophenol, 4-nitrothiophenol, and 4-methoxythiophenol.

The 2-(4-chlorophenylthio)benzoic acid precipitated is isolated by filtration, washed with water and dried.

Yield: 290.2 g (95% of theory, with reference to 4-chlorothiophenol)

Degree of purity: 96% (HPLC)

Melting point: 230°–235° C.

The product is outstandingly suitable for the preparation of pure 2-chlorothioxanthone by acid cyclization.

COMPARISON EXAMPLES

If a process according to the instructions for Example 1 is used, but employing 92 g of sodium hydroxide or 123 1 g of potassium hydroxide instead of 96.4 g of lithium hydroxide monohydrate, the following results are obtained.

| Alkali metal hydroxide employed | Yield of I, with respect to 4-chloro-thiophenol (% of theory) | Purity of I in the crude material obtained | Melting point (°C.) |
| --- | --- | --- | --- |
| NaOH | 54 | 65% | 170–198 |
| KOH | 52 | 59% | 190–198 |

In the following table, further 2-arylthiobenzoic acids are shown, which can be prepared according to the instructions for Example 1 by the reaction of lithium 2-chlorobenzoate with lithium thiophenoxides.

The table indicates:

in column 1: the employed thiophenol of the formula V in column 2: the 2-arylthiobenzoic acid of the formula I obtained in column 3: the yield of I, with reference to the thiophenol employed in column 4: the melting point of the 2-arylthiobenzoic acid obtained.

| | 2-Arylthiobenzoic acids from lithium 2-chlorobenzoate and lithium thiophenoxides | | | |
| --- | --- | --- | --- | --- |
| Example | Thiophenol (V) | 2-Arylthiobenzoic acid (I) | Yield (% of theory) | Melting point (°C.) |
| 2 | 4-Methylthiophenol | 2-Phenylthiobenzoic acid | 85 | 164–167 |
| 3 | 4-Fluorothiophenol | 2-(4-Fluorophenylthio)benzoic acid | 86 | 172–170 |
| 4 | 4-Methylthiophenol | 2-(4-Methylphenylthio)benzoic acid | 89 | 210–215 |
| 5 | 4-Isopropylthiophenol | 2-(4-Isopropylphenylthio)benzoic acid | 85 | 148–152 |
| 6 | 2-Chlorothiophenol | 2-(2-Chlorophenylthio)benzoic acid | 80 | 169–172 |
| 7 | 4-Methoxythiophenol | 2-(4-Methoxyphenylthio)benzoic acid | 83 | 225–229 |
| 8 | 4-Chloro-2,5-dimethylthiophenol | 2-(4-chloro-2,5-dimethylphenylthio)-benzoic acid | 84 | 182–185 |
| 9 | 4-Nitrothiophenol | 2-(4-Nitrophenylthio)benzoic acid | 80 | 221–225 |
| 10 | 3-Trifluoromethylthiophenol | 2-(3-Trifluoromethylphenylthio)-benzoic acid | 83 | 149–153 |

EXAMPLE 1

2-(4-Chlorophenylthio)benzoic acid 96.4 g of lithium hydroxide monohydrate are added to a mixture of 144.6 g of 4-chlorothiophenol and 172.2 g of 2-chlorobenzoic acid in 450 g of tetralin and the mixture is heated to 185°–190° C. in a water separator to remove about 54 ml of water of reaction.

The reaction mixture is subsequently stirred at 185°–190° C. for 8 hours, cooled to 115° C. and added to 500 ml of water.

The aqueous product phase is separated off, diluted using 1.5 l of water and adjusted to pH 2 by the addition of 125 g of 30% strength hydrochloric acid.

What is claimed is:

1. Process for the preparation of 2-arylthiobenzoic acid of the formula

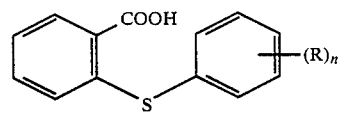

wherein

R is alkyl having 1 to 4 carbon atoms, alkoxy having 1 to 4 carbon atoms, trifluoromethyl, hydrogen, fluorine, chlorine or nitro and n is 1, 2, 3 or 4, and when n is 2, 3, or 4, each R can be identical or different, which comprises reacting lithium 2-chlorobenzoate of the formula

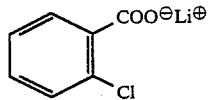

with lithium thiophenoxide of the formula

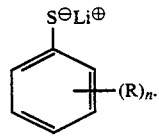

2. Process according to claim 1, wherein the reaction temperature is from 140° C. to 220° C.

3. Process according to claim 1, wherein the reaction temperature is from 170° C. to 200° C.

4. Process according to claim 1, wherein the amount of lithium 2-chlorobenzoate is about 1 mole per mole to 1.5 moles per mole of lithium thiophenoxide.

5. Process according to claim 1, wherein the amount of lithium 2-chloro-benzoate is about 1.1 moles per mole to 1.3 moles per mole of lithium thiophenoxide.

6. Process according to claim 1, wherein the reaction is carried out in an aprotic solvent.

7. Process according to claim 6 wherein the solvent is p-xylene o-xylene, m-xylene, mesitylene, chlorobenzene, o-chlorotoluene, o-dichlorobenzene, tetralin, solvent naphtha toluene dibutyl ether, diphenyl ether, dimethylformamide, dimethylacetamide, N-methylpyrrolidone, N,N-dimethylpropyleneurea, dimethyl sulfoxide or dimethylaniline.

8. Process according to claim 1, wherein the reaction is carried out in the melt without a solvent.

9. Process according to claim 1, wherein the lithium thiophenoxide is of the formula

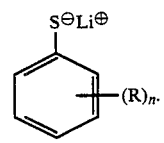

10. Process according to claim 9 wherein the lithium thiophenoxide is of the formula

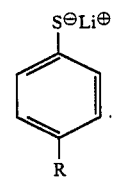

11. Process according to claim 1 wherein the lithium thiophenoxide is of the formula

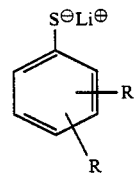

wherein the two R substituents are bonded at the 2,3-, 2,4-, 2,5-, 3,4-, 3,5- or 4,5 ring positions.

12. Process according to claim 1 wherein the lithium thiophenoxide is of the formula

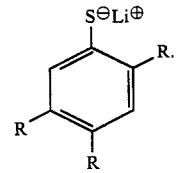

13. Process according to claim 1 wherein the lithium thiophenoxide is the lithium salt of thiophenol, 4-fluorothiophenol, 3-fluorothiophenol, 4-chlorothiophenol, 2-chlorothiophenol, 2,5-dichlorothiophenol, 4-chloro-2,5-dimethylthiophenol, 4-methylthiophenol, 4-isopropylthiophenol, 3-trifluoromethylthiophenol, 4-nitrothiophenol, or 4-methoxythiophenol.

14. Process according to claim 1 wherein the reaction time is from about 2 hours to 8 hours.

* * * * *